(12) United States Patent
Li

(10) Patent No.: US 9,714,888 B2
(45) Date of Patent: Jul. 25, 2017

(54) APPARATUS FOR FAST HIGH PRESSURE SYNGAS SAMPLING

(71) Applicant: Ye Li, Birmingham, AL (US)

(72) Inventor: Ye Li, Birmingham, AL (US)

(73) Assignees: Wanwang Peng, Birmingham, AL (US); Ye Li, Birmingham, AL (US)

( * ) Notice: Subject to any disclaimer, the term of this patent is extended or adjusted under 35 U.S.C. 154(b) by 89 days.

(21) Appl. No.: 14/736,216

(22) Filed: Jun. 10, 2015

(65) Prior Publication Data

US 2016/0349154 A1 Dec. 1, 2016

(30) Foreign Application Priority Data

May 29, 2015 (CN) ...................... 2015 2 0359235 U

(51) Int. Cl.
*G01N 1/22* (2006.01)

(52) U.S. Cl.
CPC ... *G01N 1/2247* (2013.01); *G01N 2001/2238* (2013.01); *G01N 2001/2282* (2013.01)

(58) Field of Classification Search
CPC ................ G01N 1/2247; G01N 2001/2282
See application file for complete search history.

(56) References Cited

U.S. PATENT DOCUMENTS

| 6,139,801 | A | * | 10/2000 | Kawachi | ............. | G01N 1/2273 |
| | | | | | | 422/110 |
| 2006/0172428 | A1 | * | 8/2006 | McDermott | ......... | G01N 1/2205 |
| | | | | | | 436/63 |
| 2015/0065901 | A1 | * | 3/2015 | Bhatnagar | ............. | A61B 5/082 |
| | | | | | | 600/532 |

\* cited by examiner

*Primary Examiner* — Hezron E Williams
*Assistant Examiner* — David Z Huang

(57) ABSTRACT

The invention discloses a device and method for rapid high-pressure gas sampling includes a main gas line, a sample container filled with liquid and sampling tube, a close loop sampling bypass line coupled with the said main gas line, the upper end of the sampling tube connects with a particulate filter in the sampling bypass line, the sampling tube lower end extending into inside sample container, on top of the sample container a gas outlet line is attached, condensate drain path attaches to the sample container. The fast high pressure gas sampling device significantly minimizes the process gas sampling time to a few seconds range, which will help improve a real-time gas components analysis and process control for high pressure high temperature and dust laden conditions.

12 Claims, 1 Drawing Sheet

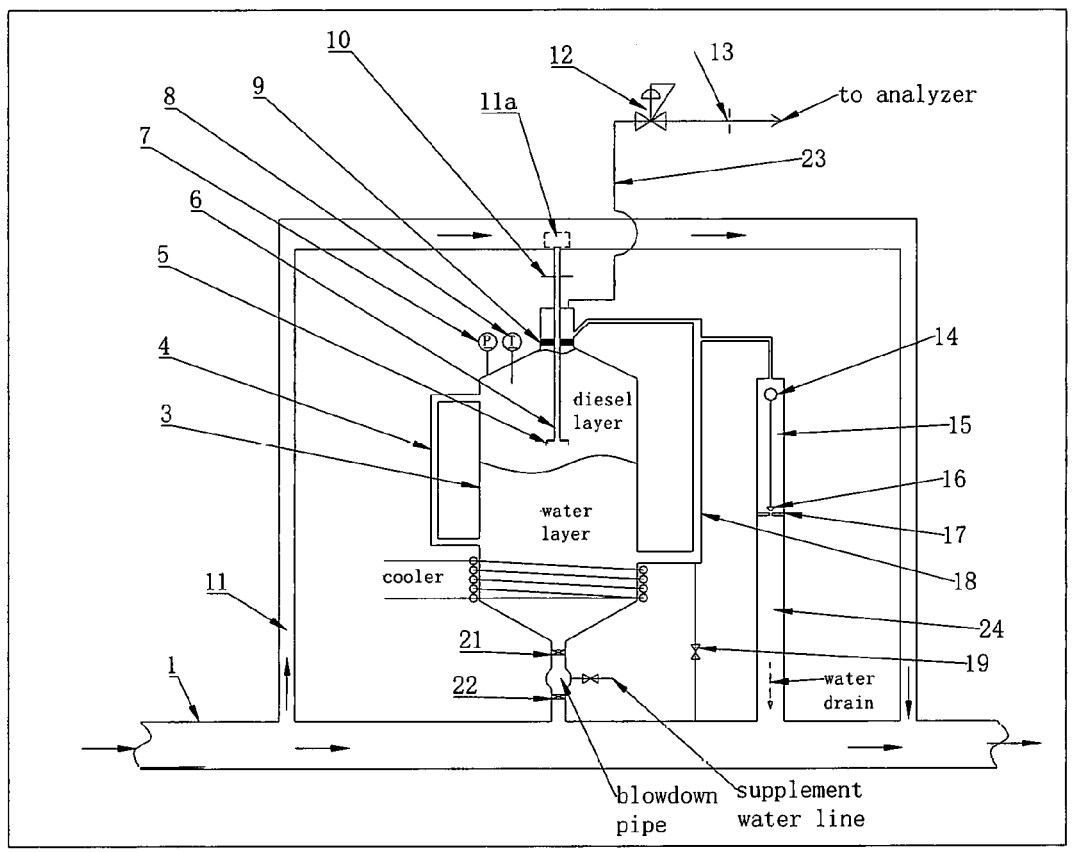

APPARATUS FOR FAST HIGH PRESSURE SYNGAS SAMPLING

FIELD OF INVENTION

The invention relates to the field of chemical detection technology, in particular to a high-pressure syngas fast sampling devices.

BACKGROUND ART

High pressure gasification processes for syngas production require regular component analysis using a range of instruments. The technique used in gas sampling inherently has a lag time and this impacts on operational management of the process. In some coal gasifiers (such as a fluidized bed gasifier outlet or multiple stage entrained bed gasifier) syngas often contains other organic components such as polyaromatic hydrocarbons (e.g. naphthalene, phenanthrene, anthracene). Syngas is typically cooled down before analysis, as a result these components change from vapor phase to liquid condensate or even solid crystals. Typically, an indirect cooler with a metal surface for heat transfer is used. During gas cooling through said cooler, organic components will deposit on the cooling surface. This affects further cooling and periodic regeneration of the surface by heat or chemical means is required during normal operation. The sampling device is used in batch wise mode. A drawback with current sampling methodology is the significant lag time, due to large cooler volume relative to the sampling gas flow rate resulting in the on-line analysis being unsuitable for real time on-line monitoring and process control.

Accordingly, there is a need for improved analytical methodology to overcome the above limitations.

SUMMARY OF THE INVENTION

To overcome the shortcomings and problems of the prior art, the invention provides a fast high-pressure syngas sampling device capable sampling high pressure, high temperature and dust laden gas.

A fast high-pressure syngas fast sampling apparatus includes a main gas line, a sample container filled with liquid and sampling tube, a close circuit bypass gas line is coupled with the main gas line. The upper end of the sampling tube is connected with a bypass gas line. The lower end of sampling tube is inserted into the sample container, The top of the sample container is connected to the gas outlet pipe. The bottom of the sampling tube is attached to a gas distributor.

A high pressure flow restriction orifice is also attached to the upper portion of the sampling tube. The particulate filter inside the sampling bypass gas line is connected with the sample tube start point.

The upper portion of the sample container has a built-in defogger.

The gas outlet pipe is connected with a pressure regulator and a low pressure flow restriction orifice.

The sample container is equipped with a blowdown pipe at the bottom of sample container with two valves to form a blowdown volume between two valves. A water supplement line is connected to the blowdown volume.

The sample container is also provided with an overflow pipe, the lower part of the overflow pipe is connected to the lower portion of the sample container. The upper end of the overflow pipe connected to the upper portion of the sample container, a manual drain valve is attached to the overflow pipe bottom.

The drain pipe is connected to the side of overflow pipe, the drain tube is equipped with a solution chamber, the chamber has a valve seat with drain holes, a float ball is present in the solution chamber, and the valve part is attached to the float ball. The valve part matches with the valve seat. The drain pipe is tied to the main gas line.

The sample container possesses cooling coils, the cooling coils are suitable for air expansion or water based cooling.

The container further comprises a level indicator, pressure gauge and a thermometer.

The fast high-pressure sampling device is suitable for use in a high pressure gasifier for syngas production process, in a timely manner to take and send syngas samples for analysis. Sampling time is short, starting with liquid medium as a coolant and uses absorbents for polyaromatic hydrocarbon absorption. It is applicable to high pressure, high temperature organics containing syngas sampling, also it is used for the syngas containing a small amount of fine dust occasions. The invention can be widely used in plants with pressurized fixed bed gasifiers, a fluidized bed gasifiers and entrained bed gasifiers.

BRIEF DESCRIPTION OF THE DRAWINGS

The accompanying drawing(s), which are incorporated in and constitute a part of this specification, illustrate several aspects described below.

FIG. 1 is a schematic diagram of piping connections of this invention.

DETAILED DESCRIPTION OF THE PREFERRED EMBODIMENTS

It must be noted that as used herein and in the appended claims, the singular forms "a", "an", and "the" include plural referents unless the context clearly dictates otherwise. Thus, for example, reference to "a compound" includes a plurality of compounds.

I. DEFINITIONS

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 10%, 5% or 1%, or any subrange or subvalue there between.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a device or method consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

One aspect of the invention is described in further detail below with reference to the drawings.

As shown in FIG. 1, a fast high-pressure syngas sampling apparatus, comprising a main gas line 1, a sample container 3 filled with liquid and sample tube 6, a closed circuit of bypass gas line 11 is coupled with the main gas line 1. The upper end of the sample tube 6 is connected with bypass gas line 11, the sampling tube 6 extends into the inside of the sample container 3, on top of the sampling container 3 is gas outlet pipe 23. A gas distributor 5 is attached to the bottom of the sampling tube 6, syngas flows through the gas distributor thus dispersing more evenly into the liquid. The gas outlet pipe 23 is connected with the pressure regulator 12 and a low pressure orifice 13. The pressure regulator regulates the cooled sample gas pressure and keep it stable for analytical sampling, the low pressure orifice prevents sudden gas flow increases which would otherwise result in the loss of liquid entrainment. Low pressure clean syngas passes through the pressure regulator and flows at higher velocity at low pressure to analytical instruments house for various syngas components analysis.

A high pressure limiting orifice 10 is attached to the upper part of the sampling tube 6. Sample bypass line 11 is provided on the particulate filter 11a, the upper end of sampling tube 6 is connected to the particulate filter. Syngas from sampling the bypass line flows through the particulate filter and high pressure limiting orifice before entering the sampling container. Particulate filters are used to filter out large particles in the syngas. The upper narrowed neck section of the sampling container 3 has a built-in demister 9, the cooled syngas passes through the demister before leaving the sample container top.

In addition, the sampling container 3 is also provided with an overflow pipe 18. The lower part of the overflow pipe 18 is connected to the lower portion of the sample container 3. The upper end of the overflow pipe 18 is connected to the upper portion of the sample container. A manual drain valve 19 is also attached to the overflow pipe 18. The overflow pipe 18 is connected to the drain pipe 24, the drain pipe 24 is also equipped with a solution chamber 15 which features a liquid-repellent seat 17 with drainage holes. The solution chamber 15 is equipped with a float ball 14, which is connected to the liquid-repellent part 16, the part 16 matches with liquid-repellent seat 17. The drain pipe 24 communicates with the main gas line. If sample container becomes too full the liquid will be discharged through the overflow pipe into the drain pipe. As the solution level of liquid chamber rises, the float moves up, which drive the valve resulting in liquid being discharged through the valve opening into the main gas line. As the solution level in drain pipe is reduced, the float drops down and the valve returns back to being a small opening or closed.

In addition, the bottom of the sample container is provided with blowdown pipe, with upper valve 21 and the lower valve 22, and with a liquid supplement pipe between the valves. Any unclean liquid and/or solid in the sampling container can be discharged via the blow down pipe. Wherein the syngas contains a small amount of fine dust, the dust will also be sampled into the sample container in contact with the liquid, any dust is washed to the bottom of the sample container The two valves of blowdown pipe will exclude the possibility of solids in the sample container.

By using the blowdown pipe and two valves in cyclic mode, any sludge at the bottom of the container is discharged to the main gas pipeline. During normal operation, the upper valve opens and the blowdown volume is filled with sludge, after a certain period of time, the upper valve is turned off and the bottom valve opened, the whole volume of water and sludge is discharged, then the bottom valve is closed. A supplemental water line is used to fill the blowdown volume, the water line is then closed, and the top valve opened to begin a new cycle. In most cases, together with the condensate overflowing, the overflow pipe may withdraw the most part of sludge collected in the sample container.

The sample container 3 has a sidewall cooling device, the cooling device can be an air or water cooler. The cooler maintains the container liquid temperature to prevent any temperature rise due to contact with the hot gases. Since the gas flow rate is small, about 5~20 l/min, while the volume of the liquid container is large, the applicable temperature of sample gas source may be higher, the hot gas may sampled without the need for additional cooling treatment. Gas temperature suitable for sampling is about 50~750° C., as long as the piping material is configured appropriate temperature may also be higher. The syngas source pressure may be about 0.2~10 MPa.

In addition, the sample container 3 has a level display meter 4, a pressure gauge 7 and a thermometer 8. The level display meter provides a real-time view into the level of organic absorbents and condensate water. The pressure gauge and thermometer, provide real-time working pressure and fluid temperature measurements.

Typically the liquid in sample container is filled with absorbent such as diesel and other organic additives, the liquid in the container is filled as full as possible. Absorbents such as diesel after prolonged use need regular (eg weekly) replacement and replenishing. Since the density of absorbent diesel is lower than the density of water the diesel remains in the upper layer of the sampling container, while the water forms the lower layer. A portion of the syngas from the main flow line is side lined through a bypass line, a small fraction of syngas is sampled and flows through the particulate filter and high pressure limiting orifice into the inner sampling tube, then into the sample container. The syngas sample is cooled while in direct contact with liquid in the vessel, water vapor contained in the gas sample is condensed into water, potential polyaromatic hydrocarbons are liquefied or solidified. For example, benzene liquefies, while larger molecules such as naphthalene, phenanthrene condense out and under normal conditions becomes crystalline, but because of their solubility in absorbents such as diesel in cold condition, organic components such as these polyaromatic hydrocarbons dissolved in diesel to form a homogeneous liquid. The diesel absorbent has significantly lower density than water, therefore the diesel and organic components remain located in the top of the container, whilst the water stays in the lower lay. In the general case, the syngas has condensable organics content about 0.1 to 2%, and the water vapor content can be about 2% to 50%. With gas sampling, an increase in the organic content in diesel is slow, while the condensed water is accumulated relatively quickly. By using the overflow mechanism automatically, the condensed water from vessel low layer is exported outside the sampling container, so as the liquid level within the sample container remains unchanged. Condensate drained from the sampling system returns to the syngas main line. Potential dust contained in the syngas sample is washed out and removed from vessel together with condensate draining.

In the sampling vessel, the syngas is cooled by the liquid, it then rises to the top of the sample container, the demister provides gas-liquid separation, then the synthesis gas passes through the pressure regulator and the pressure is controlled to ensure stable pressure for the analytical instruments used. The low pressure gas line orifice prevents sudden gas flow increases, which may result in the loss of liquid entrainment. Low pressure clean synthesis gas flows at higher velocity through the pipeline to gas analyzer for composition analysis.

The sampling device may be used at high pressure or low pressure. When the source gas is dust free, the high pressure flow restriction orifice is used to let down pressure, then the sampling device is preferably operated at low pressure, which even further facilitates the reduction of sampling time. When the source gas contains dust, the dust laden gas is allowed to enter the sampling device. In this case, sampling device is preferably used at high pressure by using pressure regulator to prevent any drop in pressure.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

What is claimed is:

1. A fast high-pressure syngas sampling device, the sampling device comprising:
    a main gas line transporting process gas flow,
    a bypass gas line connected to the main gas line to form a closed circuit, wherein the bypass line is positioned above the main gas line,
    a sampling container filled with two liquids, and the sampling container is located between the bypass line and the main gas line,
    a sampling tube with one end inserted into the top section of the sampling container, and a second end connected to the horizontal section or the vertical section of the bypass gas line,
    a sample gas outlet pipe connected to the top of the sampling container,
    an overflow pipe located beside the sampling container, wherein the overflow pipe bottom is connected to the lower portion of the sampling container, and wherein the overflow pipe top is connected to the top section of the sampling container, and
    a drain pipe having an inlet and an outlet, wherein the inlet is connected with the upper section of the overflow pipe, wherein the outlet is connected with the top of the main gas line,
    a blowdown pipe connected to the bottom of the sampling container, wherein the blowdown pipe is also connected with the top of the main gas line.

2. The syngas sampling device according to claim 1, wherein a gas distributor is attached to the bottom of the sampling tube.

3. The syngas sampling device according to claim 2, wherein the upper portion of the sampling tube is equipped with a high pressure flow restriction orifice, and the upper end of the sampling tube is connected to a particulate filter positioned inside the bypass gas line.

4. The syngas sampling device according to claim 3, further comprising a demister installed inside the upper section of the sampling container, wherein a sample gas outlet pipe is connected to the top of the sampling container.

5. The syngas sampling device according to claim 4, wherein the sample gas outlet pipe comprises a pressure regulator and a low pressure flow restriction orifice.

6. The syngas sampling device according to claim 5, wherein the blowdown pipe comprises two valves to form a blowdown volume, wherein a water supplement line is connected with the blowdown volume, and the blowdown volume is connected with the top of the main gas line.

7. The syngas sampling device according to claim 6, wherein the overflow pipe bottom is also attached to the top of the main gas line with a manual drain valve.

8. The syngas sampling device according to claim 7, wherein the overflow pipe is connected to the drain pipe, the inside of the drain pipe is equipped with a solution chamber and a liquid repellent seat, a liquid repellent part, which acts as a drain valve, is situated above the liquid repellent seat inside the drain pipet, and the bottom outlet of the drain pipe is connected with the top of the main gas line.

9. The syngas sampling device according to claim 8, wherein the sampling container sidewall comprises a cooling means, wherein the cooling means is an air cooler or a water cooler.

10. The syngas sampling device according to claim 9, wherein the sampling container comprises a level display, a pressure gauge and a thermometer.

11. The syngas sampling device according to claim 10, wherein the sampling container holds two liquids, having different densities, wherein the two liquids exhibit two layers inside the sampling container, wherein the upper layer liquid is a solvent, and the lower layer liquid is water or moisture condensate.

12. A fast high-pressure syngas sampling device, the sampling device comprising:
    a main gas line transporting process gas flow,
    a bypass gas line connected with the main gas line to form a closed circuit,
    a sampling container filled with liquids,
    a sampling tube inserted into the top of the sampling container, wherein the sampling tube is also connected with the bypass gas line,
    a sample gas outlet pipe connected with the top of the sampling container,
    an overflow pipe connected to one side of the sampling container at both the upper and the lower sections of the sampling container,
    a drain pipe connected to the upper section of the overflow pipe, wherein the drain pipe bottom is connected to the top of the main gas line,
    a blowdown pipe connected to the bottom of the sampling container, wherein the blowdown pipe is further connected with the top of the main gas line,
    a cooler attached to the sampling container,
wherein the fast high-pressure syngas sampling device is characterized by,
    a sampling operation in which:
        the sampling container is loaded with a liquid of water and a liquid of solvent, and wherein the solvent is on the upper layer and the water is on the lower layer,
        a stream of the pressure process gas flows through the main gas line, wherein a slip stream of the same type of gas flows through the bypass gas line,
        an amount of sample gas continuously flows though a particulate filter inside the bypass gas line, and passes through the sampling tube, then enters the sampling container,
        the sample gas contacts with liquids inside the sampling container, wherein the sample gas is cooled down, wherein liquefied or solidified polyaromatic hydrocarbons from the sample gas are dissolved into the upper layer of the solvent, and a moisture condensate joins the lower layer of water to make a certain amount of extra water, the extra water increases the liquid level in the sampling container and the overflow pipe, the extra water in the overflow pipe overflows into the drain pipe, the water coming from the overflow pipe increases the water level in the drain pipe, a float ball rises, a liquid repellent part, which acts as a drain valve, is lifted by the float ball, the water flows through a liquid repellent seat, which acts as the drain valve seat, and enters the main gas line, the liquid level of the sampling container is maintained constant by continuously discharging the extra water, all the moisture condensate water from the sample gas is continuously discharged into the main gas line, the water is carried away by the process gas, wherein the sample gas flowed through the liquid layers and passed through a demister is a stream of clean sample gas, the clean sample gas exits the top of the sampling container and enters the sample gas outlet pipe, a pressure regulator drops the clean sample gas pressure, wherein the clean sample gas exits the sample gas outlet to different types of analyzers, the liquids fill the the sampling container, the cooler continuously cools the sampling container and the liquids inside the sampling container, the pressure in the main gas line is in the range of 0.2 to 10 MPa, and the temperature is in the range of 50~750° C.

\* \* \* \* \*